US 9,228,867 B2

(12) United States Patent
Clarke et al.

(10) Patent No.: US 9,228,867 B2
(45) Date of Patent: Jan. 5, 2016

(54) APPARATUS FOR CHARACTERISING A FLOW THROUGH A CONDUIT

(71) Applicant: Teledyne Limited, West Drayton (GB)

(72) Inventors: Daniel Clarke, Brighton (GB); Barry John Hemblade, Hove (GB)

(73) Assignee: Teledyne Limited (GB)

( * ) Notice: Subject to any disclaimer, the term of this patent is extended or adjusted under 35 U.S.C. 154(b) by 82 days.

(21) Appl. No.: 14/351,058

(22) PCT Filed: Oct. 11, 2012

(86) PCT No.: PCT/GB2012/000785
§ 371 (c)(1),
(2) Date: Apr. 10, 2014

(87) PCT Pub. No.: WO2013/054080
PCT Pub. Date: Apr. 18, 2013

(65) Prior Publication Data
US 2015/0177033 A1    Jun. 25, 2015

(30) Foreign Application Priority Data
Oct. 13, 2011    (GB) .................................. 1117707.0

(51) Int. Cl.
*G01F 1/37*    (2006.01)
*G01F 1/56*    (2006.01)
*G01F 1/68*    (2006.01)
*G01F 1/66*    (2006.01)
*G01F 1/34*    (2006.01)

(52) U.S. Cl.
CPC .. *G01F 1/56* (2013.01); *G01F 1/34* (2013.01); *G01F 1/666* (2013.01); *G01F 1/68* (2013.01)

(58) Field of Classification Search
CPC ............. G01F 1/37; G01F 1/22; G01F 15/00; G01F 1/716
USPC ................. 73/861.52, 861.77, 861.53, 861.08
See application file for complete search history.

(56) References Cited

U.S. PATENT DOCUMENTS 4,282,883 A * 8/1981 Yerushalmy ................... 600/539
4,638,672 A * 1/1987 McCall ........................ 73/861.52
5,531,103 A    7/1996 Eaton
(Continued)

FOREIGN PATENT DOCUMENTS

GB    2180068 A    3/1987
WO    9810249    3/1998

*Primary Examiner* — Jewel V Thompson
(74) *Attorney, Agent, or Firm* — Valenti, Hanley & Robinson, PLLC; Kevin T. Duncan

(57) ABSTRACT

There is described an apparatus for characterizing a flow through a conduit. The apparatus comprises a body portion, and first and second sensors. The body portion has a longitudinal axis extending between first and second body portion ends. The cross-sectional area of the body portion varies along the longitudinal axis. In use, the body portion is arranged to be disposed substantially longitudinally within the conduit with the first body portion end disposed upstream of the second body portion end. The first sensor is disposed at or near the first body portion end. The second sensor is longitudinally spaced from the first sensor. The body portion has a larger cross-sectional area at the second sensor than at the first sensor such that, in use, the second sensor experiences an accelerated flow as compared to the first sensor. The first and second sensors are operable to sense a common variable, thereby enabling the effects of accelerated flow on the common variable to be characterized.

18 Claims, 2 Drawing Sheets

(56) References Cited

U.S. PATENT DOCUMENTS

| | | | |
|---|---|---|---|
| 5,880,378 A * | 3/1999 | Behring, II | 73/861.53 |
| 6,487,919 B1 * | 12/2002 | Edwards | 73/861.77 |
| 7,878,047 B2 | 2/2011 | Hemblade | |
| 2007/0157738 A1 * | 7/2007 | Hughes et al. | 73/861.52 |
| 2010/0326654 A1 * | 12/2010 | Hemblade | 166/250.01 |

* cited by examiner

APPARATUS FOR CHARACTERISING A FLOW THROUGH A CONDUIT

FIELD OF THE INVENTION

The present invention relates to an apparatus for characterising a flow through a conduit. Such an apparatus may be used, for example, to monitor and characterise the flow through oil or gas pipelines. In particular, the combined impact of corrosion, erosion and sand may be monitored and characterised.

BACKGROUND OF THE INVENTION

The technical and commercial threats posed by solids (sand) and the corrosivity of fluids produced from the reservoir formation are well known to oil and gas operating companies and asset managers. Proactive strategies are required to manage the impact of these solids and corrosive fluids on production and to maximise productivity. Solids production is typically episodic and can cause extreme damage almost instantaneously. Corrosive fluids can also be episodic due to water breakthrough. The consequences can include reservoir damage, erosion of choke valves, erosion and accelerated corrosion of pipework, reduction of corrosion inhibitor performance and the filling of Separators: all resulting in reduced productivity. Reliable instantaneous management of solids in offshore and subsea systems is of vital importance.

At present a number of independent discrete sensors are used to monitor corrosion, erosion and sand individually in oil and gas pipelines. The various sensors are often provided by different manufacturers, and the measurements taken by different sensors are not easily correlated. Relevant prior art is described in U.S. Pat. No. 6,946,855 (Hemblade), U.S. Pat. No. 7,878,047 (Hemblade) and US Patent Publication No. 2010/0326654 (Hemblade).

In U.S. Pat. No. 6,946,855, an apparatus is disclosed for monitoring the effect on a material of exposure to a fluid, and thereby monitoring the effect on a section of pipe for carrying the fluid. The apparatus includes a sensor element exposed to the fluid and formed as a ring of the material coaxially mounted within, but electrically insulated from, the section of pipe. Changes in the electrical resistance of the sensor element are monitored. Preferably, the apparatus also includes a reference element electrically insulated from the pipe, electrically connected in series to the sensor element and protected from exposure to the fluid. The elements may both be made from the same material as the pipe and, as they are contained within it, experience the same temperature and pressure variations as the pipe. In this manner a change in the resistance of the sensor element caused by corrosion/erosion by the fluid accurately indicates the degree of corrosion/erosion of the pipe carrying the fluid.

In U.S. Pat. No. 7,878,047, there is described an apparatus for monitoring particles in a fluid stream, comprising a body portion and a detector element that is acoustically decoupled from the body portion. The detector element comprises a target surface, a sample acoustic sensor and a corrosion sensor. The sample acoustic sensor is acoustically coupled to the target surface and is arranged to provide a first signal, which varies in dependence upon acoustic noise generated by impacts of particles and fluid on the target surface. The corrosion sensor is arranged to provide a second signal, which varies in dependence upon corrosion and/or erosion of the target surface. A corresponding method of monitoring particles in a fluid stream is also described. The method and apparatus are suitable for monitoring sand in oil and gas production flow streams.

In US Patent Publication No. 2010/0326654, an apparatus monitors a production flow from a gravel pack into a tubular sand screen disposed concentrically around downhole production tubing in an oil or gas well. A tubular sample layer is disposed concentrically around the sand screen to be exposed to the radial production flow in use. The sample layer is electrically insulated from the production tubing in use. An erosion sensor provides a signal which varies in dependence upon an electrical resistance of the sample layer, which is related to the erosion of the sample layer. An apparatus also monitors a substantially longitudinal production flow through downhole production tubing in an oil or gas well. A method and apparatus are used to monitor the condition of a gravel pack within an oil or gas well. Other methods monitor temperature or pressure conditions within an oil or gas well.

There is a need for tools for the corrosion management of produced fluids, sand management prediction and quantification, integrated modelling and chemical optimisation.

The present invention seeks to provide an improved apparatus for characterising a flow through a conduit which provides various advantages over those of the prior art, including reduced capital expenditure opportunities and improved correlation and performance for the operator. In addition, the present invention aims to improve characterisation of the hydrocarbon production stream in terms of asset integrity and flow assurance in order to enable operators to accelerate production, extend asset life, reduce intervention costs.

SUMMARY OF THE INVENTION

According to a first aspect of the present invention, there is provided an apparatus for characterising a flow through a conduit. The apparatus comprises a body portion and first and second sensors. The body portion has a longitudinal axis extending between first and second body portion ends. The cross-sectional area of the body portion varies along the longitudinal axis. In use, the body portion is arranged to be disposed substantially longitudinally within the conduit with the first body portion end disposed upstream of the second body portion end. The first sensor is disposed at or near the first body portion end. The second sensor is longitudinally spaced from the first sensor. The body portion has a larger cross-sectional area at the second sensor than at the first sensor such that, in use, the second sensor experiences an accelerated flow as compared to the first sensor. The first and second sensors are operable to sense a common variable, thereby enabling the effects of accelerated flow on the common variable to be characterised.

Thus, the first sensor is arranged to monitor the actual/upstream flow through the conduit, whereas the second sensor experiences an accelerated flow compared to the first sensor due to the flow restriction caused by cross-sectional size of the body portion within the conduit. Thus, the apparatus acts to artificially accelerate the flow through the conduit, enabling the effects of accelerated flow to be determined prior to increasing the actual flow speed through the conduit.

Embodiments of the present invention are used to characterise process stream influence on corrosion and erosion caused by process chemistry and produced solids and the impact of shear stress and flow velocity at the metal-solution interface.

The configuration of the apparatus creates actual and accelerated flow profiles across the array of sensors such that, for example, the performance of corrosion inhibitors under variable electrochemical conditions and sand loading can be monitored under the variable and induced accelerated flow profiles.

The apparatus of the present invention enables operators to observe effects of artificially accelerating production (shear stress) and increasing sand flux densities. This enables better predictive models of such things as corrosion inhibitor performance under variable sand loading conditions, including such metrics as inhibitor tenacity and persistency.

In a preferred embodiment, the combination of using metal corrosion and erosion metal loss sensors based on ohmic resistance measurements with piezoelectric passive acoustic measurements embedded within an intrusive conical profile provides a unique opportunity to characterize the process stream.

The apparatus is contemplated as being combined with the Ring Pair Corrosion Monitor (RPCM) platform of U.S. Pat. No. 6,946,855 (Hemblade) such that the accelerated flow regimes can be correlated with corrosion-erosion activity at the pipe wall.

Other preferred features of the present invention are set out in the appended claims.

BRIEF DESCRIPTION OF THE DRAWINGS

Embodiments of the present invention will now be described by way of example with reference to the accompanying drawings in which.

DETAILED DESCRIPTION OF A PREFERRED EMBODIMENT

Figure 1:
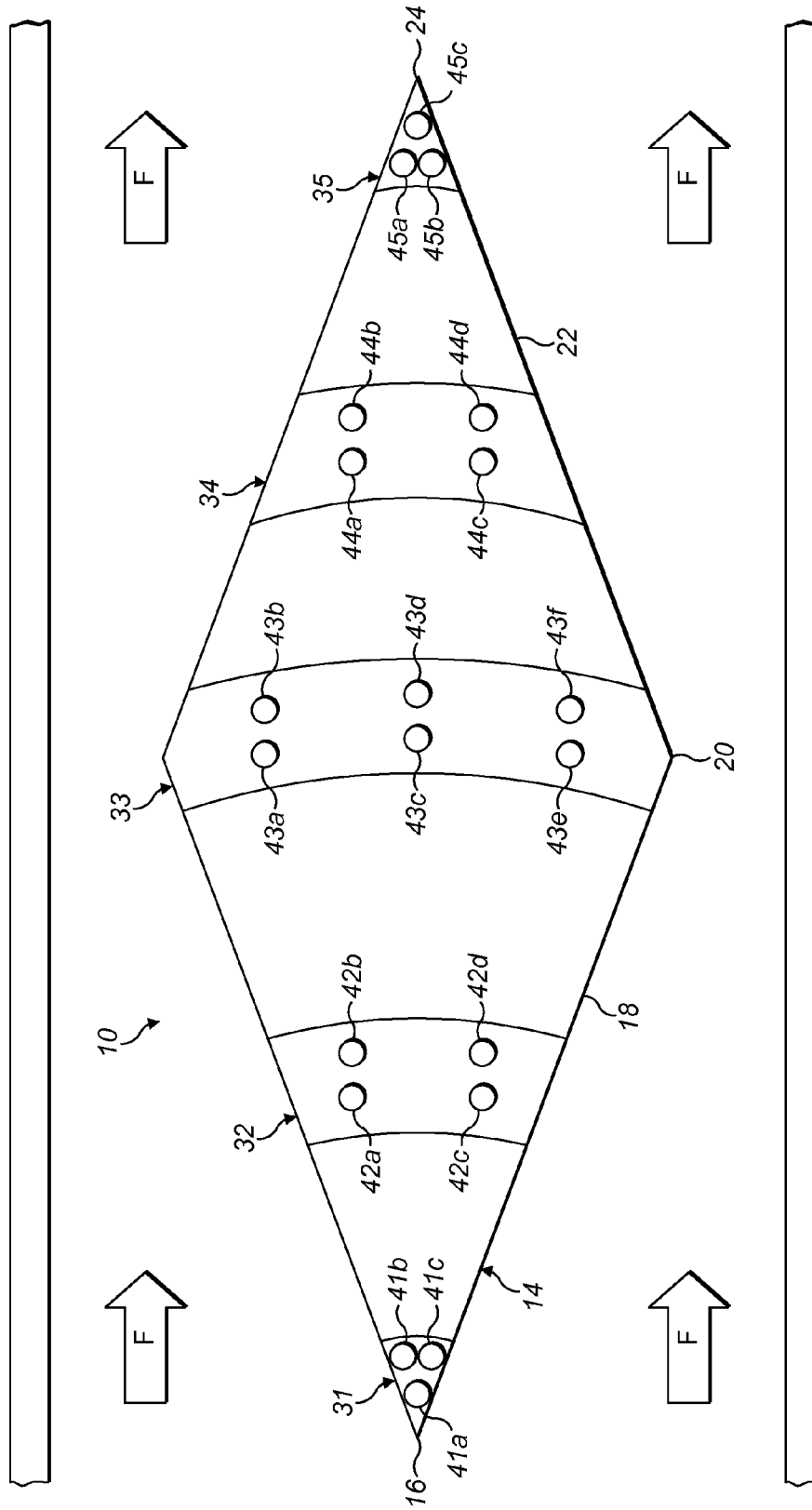
FIG. 1 is a schematic representation of a first embodiment of an apparatus for characterising a flow through a conduit.

FIG. 1 shows a first embodiment of an apparatus 10 for characterising a flow F through a cylindrical conduit 12. The conduit 12 may be an oil or gas pipeline such that the flow may include oil or gas together with entrained impurities, such as sand particles.

The apparatus 10 has a body portion 14 with a stream-wise, longitudinal axis AA' extending from an upstream end 16 to a downstream end 24. The longitudinal axis AA' of the body portion 14 is coincident with the longitudinal axis of the cylindrical conduit 12, although this is not essential. The body portion 14 has a circular cross-section at all points between the upstream and the downstream ends 16 and 24. A non-circular cross-section is envisaged in alternative embodiments, but a circular cross-section is preferred to mimic the cross-section of the circular conduit 12. The cross-sectional area of the body portion 14 varies between the upstream and downstream ends 16 and 24. In particular, the body portion 14 is effectively formed from two identical cones 18 and 22 placed with their flat circular bases against one another. The plane where the two cones 18 and 22 meet is labelled 20 in FIG. 1. This plane defines the longitudinal location at which the body portion 14 has the maximum cross-sectional area. The cross-sectional profile of the body portion 14 is symmetric between the upstream and downstream ends 16 and 24, but this is not essential. Advantageously, it would be possible to have the downstream cone 22 being longer than the upstream cone 18 in order to help prevent flow separation and to reduce losses. The cross-sectional area of the body portion 14 increases monotonically from the upstream end 16 to the central plane 20 and then decreases monotonically from the central plane 20 to the downstream end 24. (A monotonic increase in area means that the area either increases or stays the same as you move from one end to the other, with no sections of decreasing area.) The decrease in size in the latter half 22 of the body portion 14 creates a divergent flow which provides a smooth flow transition from the body portion 14 to the downstream undisturbed flow. In other words, there is good pressure recovery and the process may effectively be considered as reversible. This design reduces the chances of localised erosion in the conduit 12 downstream from the apparatus 10.

The apparatus 10 may be mounted within the conduit 12 by means of one or more mounting fins (not shown) extending radially outwards from the body portion 14. Such mounting fins may be shaped so as to disturb the flow F through the conduit 12 as little as possible (e.g. using an aerofoil design). One or more of the mounting fins may be partially hollow so as to convey electrical wires from the apparatus 10 to a location external to the conduit 12. Alternatively, the apparatus 10 may not be fixed to the conduit 12, but may be dropped off at and retrieved from a specific location in the conduit 12 by means of a pig. In this case, the apparatus 10 could be battery powered and data logging could be provided within the apparatus 10 itself, thereby negating the need for external wiring. A further alternative would be for the apparatus 10 to be more permanently fixed on a pig. A further alternative could be to provide power and communications to the apparatus 10 by wireline for downhole monitoring.

Arrangement of Sensors

The body portion 14 has a continuous outer surface. There are sensors distributed across the outer surface of the body portion 14 in order to take measurements associated with the flow F through the conduit 12. In the embodiment of FIG. 1, the sensors are arranged to form five distinct sensor arrays 31-35 in bands around the body portion 14. In alternative embodiments, there may be different numbers of sensor arrays. The use of annular (or "ring") sensor arrays allows for easier sealing of the electronics. However, the sensor arrays need not be formed in circular bands around the body portion 14. It should be noted that the "sensor array" terminology is purely for the purposes of illustration. In practice, the sensors may not be distributed in "arrays" as such. Instead, the sensors may be mutually spaced across the entire body portion 14. Many sensor arrangements are possible within the scope of the invention as defined in the appended claims.

In the embodiment of FIG. 1, the first sensor array 31 is located at the upstream end 16 of the body portion 14. The first sensor array 31 includes a plurality of sensors 41a, 41b, 41c, etc. arranged to measure a number of different variables. The upstream end 16 of the body portion 14 is pointed to form a tip or nose, so there is not space for all of the sensors 41 in the first sensor array 31 to be disposed exactly at this tip of the body portion 14. Nonetheless, the sensors 41 are closely spaced such that they are all disposed at or near the upstream end 16 of the body portion 14. Thus, the sensors 41 in the first sensor array 31 are all arranged to measure variables relating to the actual flow through the middle of the conduit 12 upstream of the apparatus 10.

The second sensor array 32 is longitudinally spaced from the first sensor array 31. In particular, the second sensor array 32 is disposed in a narrow longitudinal band extending around the first cone 18 part-way between the upstream end 16 and the plane 20 of maximum cross-sectional area. The second sensor array 32 includes a plurality of sensors 42a, 42b, 42c, etc. Some of these sensors 42 are angularly spaced around the body portion 14. Others of these sensors 42 are at substantially the same angular location but are arranged to measure different variables, thereby enabling relationships between the different variables at a given location to be studied. The sensors 42 in the second sensor array 32 experience accelerated flow (as compared to the sensors 41 in the first sensor array 31) due to the flow restriction caused by the cross-sectional size of the body portion 14 within the conduit 12 at the second sensor array 32.

The third sensor array 33 is longitudinally spaced from the first and second sensor arrays 31 and 32. In particular, the third sensor array 33 is disposed in a narrow longitudinal band extending around the plane 20 of maximum cross-sectional area of the body portion 14. The third sensor array 33 includes a plurality of sensors 43*a*, 43*b*, 43*c*, etc. Some of these sensors 43 are angularly spaced around the body portion 14. Others of these sensors 43 are at substantially the same angular location but are arranged to measure different variables, thereby enabling relationships between the different variables at a given location to be studied. The sensors 43 in the second sensor array 33 experience accelerated flow (as compared to the sensors 41 and 42 in the first and second sensor arrays 31 and 32) due to the flow restriction caused by the cross-sectional size of the body portion 14 within the conduit 12 at the third sensor array 33. The cross-sectional area of the body portion 14 is largest at the third sensor array 33.

The fourth sensor array 34 is longitudinally spaced from the first, second and third sensor arrays 31-33. In particular, the fourth sensor array 34 is disposed in a narrow longitudinal band extending around the second cone 22 part-way between the plane 20 of maximum cross-sectional area and the downstream end 24. The fourth sensor array 34 includes a plurality of sensors 44*a*, 44*b*, 44*c*, etc. Some of these sensors 44 are angularly spaced around the body portion 14. Others of these sensors 44 are at substantially the same angular location but are arranged to measure different variables, thereby enabling relationships between the different variables at a given location to be studied. In the embodiment of FIG. 1, the distance between the second sensor array 32 and the plane 20 of maximum cross-sectional area is the same as the distance between the fourth sensor array 34 and the plane 20 of maximum cross-sectional area. Thus, the second and fourth sensor arrays 32 and 34 may be considered to be disposed at mirror-image locations if the mirror is disposed in the plane 20 of maximum cross-sectional area.

The fifth sensor array 35 is located at the downstream end 24 of the body portion 14. The fifth sensor array 35 includes a plurality of sensors 45*a*, 45*b*, 45*c*, etc. arranged to measure a number of different variables. The downstream end 24 of the body portion 14 is pointed to form a tip or nose, so there is not space for all of the sensors 45 in the fifth sensor array 35 to be disposed exactly at this tip of the body portion 14. Nonetheless, the sensors 45 are closely spaced such that they are all disposed at or near the downstream end 24 of the body portion 14. Thus, the sensors 45 in the fifth sensor array 35 are all arranged to measure variables relating to the exit flow through the middle of the conduit 12 downstream of the apparatus 10. In the embodiment of FIG. 1, the distance between the first sensor array 31 and the plane 20 of maximum cross-sectional area is the same as the distance between the fifth sensor array 35 and the plane 20 of maximum cross-sectional area. Thus, the first and fifth sensor arrays 31 and 35 may be considered to be disposed at mirror-image locations if the mirror is disposed in the plane 20 of maximum cross-sectional area.

Since the cross-sectional area of the body portion 14 varies longitudinally, the flow experienced at each of the five sensor arrays 31-35 is not the same. As mentioned above, the first sensor array 31 is arranged to monitor characteristics of the actual/upstream flow through the conduit 12. The second sensor array 32 is arranged to monitor accelerated flow characteristic due to flow restriction caused by the increased cross-sectional area of the body portion 14 within the constant diameter conduit 12. The flow is further accelerated at the third sensor array 33 where the flow restriction is greatest due to presence of the largest cross-sectional area of the body portion 14 at this location. However, the flow is thereafter decelerated at the fourth sensor array 34 and further decelerated at the fifth sensor array 35 due to the decreasing cross-sectional area of the body portion 14 which reduces the restriction of flow through the conduit 12.

In summary, the apparatus 10 includes various embedded sensors across the surface of the body portion 14. The sensors may be arranged in both longitudinal and circular (i.e. annular) arrays to detect the influence of variable flow regimes over the surface. Longitudinal arrays of sensors allow for somewhat simplified electronics, so may be advantageous in some situations. The use of sensor "arrays" is not essential. However, the sensors 41-46 are advantageous arranged in arrays such that a number of different variables may be sensed by multiple sensors at a single location. This allows a direct comparison of sensed data without the need to normalise the results based on sensor location.

Types of Sensors

Examples of process variables which may be measured by the sensors 41-45 in the sensor arrays 31-35 are as follows:
 (a) Pressure differential (e.g. upstream and downstream of the apparatus, or at entry and most restrictive point of apparatus, or otherwise)
 (b) Pressure (e.g. upstream, or otherwise)
 (c) Temperature (e.g. upstream, or otherwise)
 (d) Cumulative metal loss due to corrosion or erosion-corrosion
 (e) Cumulative metal loss due to erosion
 (f) Acoustic energy (e.g. total acoustic energy spectrum, or otherwise)
 (g) Solution conductivity
 (h) Film deposition
 (i) Conductive scales Such sensors will be familiar to a skilled person in this field.

Conventionally, corrosion is measured, for example, by an electrical resistance probe. Such a probe has a sample element that is exposed to the fluid flow such that particles entrained in the fluid flow may impact the sample element. When a particle impacts the sample element in this way, it may corrode the sample element and therefore change the thickness and hence the electrical resistance of the sample element. An electrical resistance probe therefore measures changes in the electrical resistance of its sample element in order to determine the corrosion rate.

A prior art electrical resistance probe is described, for example, in U.S. Pat. No. 6,693,445 (Sutton). In this patent, a probe is disclosed which is suitable for use with an apparatus for monitoring the corrosion of a material by accurately measuring changes in the resistance of an exposed sample element in relation to a protected reference element. The two elements are electrically connected in series via a bridge and so experience the same temperature and pressure variations. The elements are formed from the same piece of material divided by an elongate slot and are proximate to one another so that the temperature difference between them is minimal. This prevents false indications of corrosion by ensuring that the temperature coefficient of the resistivities is the same in both elements. The reference element is covered with a corrosion-resistant layer. This layer is preferably as thin as possible and also a good thermal conductor to further ensure equal temperature of the reference and exposed elements.

Acoustic sensors are used to measure the acoustic energy spectrum of the flow. Thus, solids entrained in the flow may be detected by means of particle impacts on the acoustic sensors. In one embodiment, the acoustic sensors may be piezoelectric sensors. However, this is just one exemplary implementation, and it will be understood that other types of acoustic sensors may be used when implementing the present invention. Acoustic and electrical resistance sensors and their combined use monitoring sand in oil and gas production flow streams are described in U.S. Pat. No. 7,878,047.

US Patent Publication No. 2010/0326654 describes, inter alia, the implementation of corrosion and erosion sensors and absolute and differential pressure transducers in an apparatus mounted centrally within oil/gas production tubing.

The disclosures of the above-referenced documents are incorporated herein by reference in their entirety.

In one embodiment, the apparatus 10 is set up with various sensors to monitor temperature, pressure (using absolute and differential pressure transducers), metal loss relating to corrosion and/or erosion (e.g. using electrical resistance sensors), acoustics relating to particle impacts, and conductivity. The sensors advantageously include erosion sensors based on ohmic resistance and constructed of corrosion resistant alloy steels. Such sensors may also be used to monitor deposition of conductive scales. However, there will be no corrosion signal due to the corrosion-resistant material used for manufacturing the sensing element. The sensors advantageously also include corrosion sensors based on ohmic resistance and constructed of carbon steel, which is corrodible. Acoustic sensors are also included. Each acoustic sensor has its own target surface that is acoustically decoupled from the body portion 14. Each acoustic sensor is arranged to provide a signal which varies in dependence upon acoustic noise generated by impacts of particles and fluid on its target surface. It should be noted that an acoustic sensor will provide a stronger signal if the target surface is larger. Therefore, it is desirable to locate one acoustic sensor near the plane 20 of maximum cross-sectional area. In order to increase the signal strength, the target surface of each acoustic sensor could extend annularly around the body portion 14 at a particular longitudinal location. It is also desirable to include corresponding reference acoustic sensors that are acoustically decoupled from both the body portion 14 and the relevant target surface. Each reference acoustic sensor is arranged to provide a signal which varies in dependence upon acoustic noise detected by the reference acoustic sensor. The combination of an acoustic sensor with a nearby reference acoustic sensor enables the acoustic signal from the acoustic sensor to be compensated for small temperature and pressure variations which are also present in the reference acoustic signal. See U.S. Pat. No. 7,878,047 for further details. Another desirable sensor would be an acoustic sensor coupled to the surface of the body portion 14 and arranged to generate signals proportional to the cumulative fluid and particle impacts on the surface of the body portion 14. Solution conductivity sensors would also be desirable to detect presence of conductive solutions such as formation water. It is also advantageous to include pressure differential sensors embodied within the body portion 14 to measure pressure changes along the length of the apparatus. According to Bernoulli's theorem, such pressure changes are relating to the accelerating/decelerating flow around the variable diameter body portion 14. It is particularly desirable to be able to measure pressure changes between the various sensor arrays 31-35 where the other process variables will be measured.

Measurements and Outputs

As described above, the apparatus 10 is inserted into the flow in a longitudinal direction, and the apparatus 10 has a variable conical form profile. The presence of the apparatus 10 in the conduit 12 creates a flow regime across the surface of the body portion 14 whose geometry is dictated by a configurable variable shear stress across the surface. The artificially induced flow regime enables the effects of corrosivity, erosivity and particle trajectory to be monitored. The artificially induced flow regime influences the behaviour and performance of corrosion inhibitor surfactant films, electrochemical reactions, particle erosion potential, and the cumulative acoustic energy.

In the embodiment of FIG. 1, metal loss sensors in each of the sensor arrays 31-35 enable metal loss to be measured between discrete points along the stream-wise length of the body portion 14 and at several locations around the circumference. The measurements are filtered and differentiated to provide a 2D discrete metal loss rate map over the surface of the body portion 14.

The shape of the body portion 14 is carefully designed such that the fluid velocity field and the resulting shear stress profile over the surface of the body portion 14 can be predicted using computational fluid dynamics (CFD) for any given fluid mixture and inlet velocity.

CFD (or even a simple linear prediction for incompressible flows) may be used to calculate the equivalent mean flow velocity in a conduit of interest required to reproduce the same shear stress and boundary layer conditions as seen at each location on the cone surface. The resulting function is:

$$Q_e = f(x, Q_{in}, D) \quad (1)$$

where $Q_e$ is equivalent volumetric flow rate, $Q_{in}$ is the inlet flow, x is the stream-wise distance along the surface of the body portion 14, and D is the internal diameter (ID) of the conduit of interest.

The output of the apparatus includes metal loss rates at known locations x, a pressure change value (dp) from which flow rate $Q_{in}$ can be calculated, and pressure and temperature. A function can therefore be derived using the relationship in equation (1) and accumulated measurement data to give:

$$MLR = g(Q_e, p, T) \quad (2)$$

where MLR is the metal loss rate. Such a model would provide a metal loss rate versus flow rate at any given pressure and temperature for a given process fluid and inhibitor combination. The form of function g is expected to be similar for most applications. Data from the apparatus 10 may be used to tune the function using empirical coefficients. The model would be 'self-learning' and adapt as the process conditions changed over time.

The apparatus 10 is able to provide a similar capability for sand quantification by making use of metal loss and acoustics measurements combined with CFD. The CFD results yield particle trajectories which are a necessary input to any algorithm for quantifying sand mass flux under a wide range of conditions.

In various implementations, it is envisaged that the apparatus 10 could be used to characterise the erosion risk of choke valves, to detect the sand rate, and to better understand the erosion/corrosion characteristics of the flow stream throughout the transportation system, particularly at locations such as chokes or bends.

Measuring the "Actual" Flow Through the Conduit

The first sensor array 31 is intended to monitor process variables of the "actual" flow through the conduit (i.e. the flow which would occur in the conduit 12 if the apparatus 10 were not present). The arrangement shown in FIG. 1 is suitable for measuring the "actual" upstream flow characteristics using the sensors 41 in the first sensor array 31. As an alternative, the upstream end 16 of the body portion 14 shown in FIG. 1 need not be a pointed conical tip, but could instead be slightly rounded.

Figure 2:
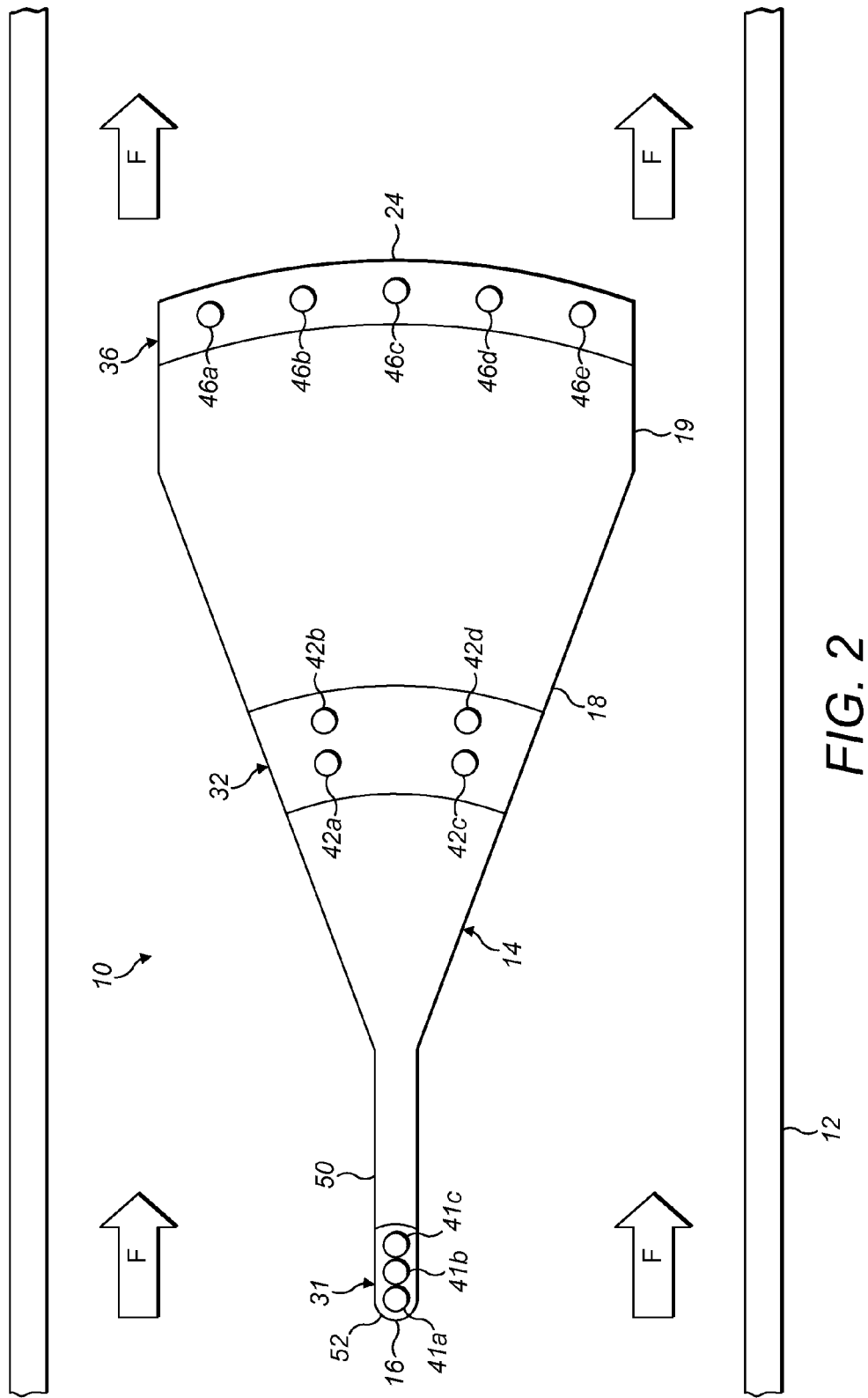
FIG. 2 is a schematic representation of a second embodiment of an apparatus for characterising a flow through a conduit.

An alternative embodiment of an apparatus 10 for characterising a flow F through a cylindrical conduit 12 is shown in FIG. 2. Assuming that the conduit 12 is substantially the same both in the region of and somewhat upstream of the apparatus 10, then the "actual" flow through the conduit 12 is the same as the flow just upstream of the apparatus 10. Thus, in the embodiment of FIG. 2, the upstream end 16 of the body portion 14 is formed as an extended longitudinal "nose" 50. The upstream end 52 of the nose 50 is rounded. The nose 50 is long and narrow, having a small cross-sectional area relative to the internal diameter of the conduit 12. This design enables the sensors 41 in the first sensor array 31 at the tip of the nose 50 to take measurements in a flow that is substantially unaffected by the presence of the apparatus 10 (i.e. the undisturbed upstream flow). Hence, the measurements are as close to that of the "actual" upstream flow as possible.

The embodiment of FIG. 2 further includes a first conical section 18 similar to that shown in FIG. 1. However, the embodiment of FIG. 2 does not include a second conical section (cf second conical section 22 of FIG. 1). Instead, the downstream end 24 of the apparatus shown in FIG. 2 is formed as a cylinder 19 having constant cross-sectional area in this longitudinal section. Thus, the flow F is substantially tangential to the body portion 14 at the cylindrical portion 19. The cylindrical portion 19 includes a downstream sensor array 36 formed as a narrow longitudinal band extending around the cylindrical portion 19 at or near the downstream end 24 of the body portion 14. The downstream sensor array 36 includes a plurality of sensors 46a, 46b, 46c, etc. Some of these sensors 46 are angularly spaced around the body portion 14. Others of these sensors 46 are at substantially the same angular location but are arranged to measure different variables, thereby enabling relationships between the different variables at a given location to be studied. The cross-sectional area of the body portion 14 increases monotonically from the upstream end 16 to the downstream end 24 in FIG. 2. Due to the abrupt change in the flow restriction within the conduit 12 at the downstream end 24 of the body portion 14, the apparatus 10 of FIG. 2 may be used to generate a downstream low pressure stagnant region for low shear corrosion measurement.

Testing the Effects of Accelerating the Flow

In order to increase the rate of oil or gas production, it would be desirable to accelerate the flow F through the conduit 12. However, acceleration of the flow may have undesirable impacts on the corrosion and/or erosion of the pipeline and choke valves, for example. Therefore, before increasing the actual flow F through the pipeline, it is desirable to fully understand the implications of such a flow increase. The present apparatus 10 allows the impacts of artificially accelerating the flow to be studied. This is accomplished by comparing measurements taken at the first sensor array 31 (relating to the actual flow) with those at the second and/or third sensor arrays 32 and 33 (relating to artificially accelerated flow regimes).

For example, all other things being equal, an acoustic sensor in the second sensor array 32 is likely to be subject to increased particle flux intensity and higher particle impact velocities than an acoustic sensor in the first sensor array 31 because of the flow restriction and accelerated flow at the second sensor array 32. Similarly, an acoustic sensor in the third sensor array 33 is likely to be subject to a greater number of particle impacts per unit time than an acoustic sensor in the second sensor array 32 because of the further accelerated flow experienced at the third sensor array 33. To provide a like-with-like comparison, the acoustic sensors in the first, second and third sensor arrays 31-33 should have sensor surfaces at the same angle of orientation with respect to the predominant flow direction. In addition, the sensor surfaces should be the same size, etc. In other words, the design of the apparatus 10, and particularly the design of the sensors in the first, second and third sensor arrays 31-33, should be such that the effects of the flow speed alone may be monitored.

The effects of accelerating the flow may also be studied using the apparatus 10 shown in FIG. 2. In particular, the sensors 42 in the second sensor array 32 are subject to an accelerated flow as compared to the sensors 41 in the first sensor array 31. The sensors 46 in the downstream sensor array 36 are subject to a further accelerated flow as compared to the sensors 42 in the second sensor array 32. Thus, the effects of accelerating the flow through the pipeline may be studied based on the artificially accelerated flows experienced at the second sensor array 32 and the downstream sensor array 36 as compared to the actual flow experienced by the first sensor array 31.

In summary, the effects of a potential increase in the flow speed within a conduit 12 may be studied using the apparatus 10. This is because the apparatus 10 itself creates a locally accelerated flow regime. Specifically, parts of the body portion 14 with a larger cross-sectional area will experience artificially accelerated flow due to the flow restriction in the conduit 12 caused by the presence of the apparatus 10. Thus, a comparison between measurements taken at an accelerated flow location and corresponding measurements taken at or near the upstream end of the apparatus 10 enables the effects of accelerated flow speed to be studied. In some cases, it is only necessary to compare one pair of actual and accelerated measurements of a given variable, but a comparison of multiple pairs of measurements will provide additional data and/or redundancy to protect against possible hardware failures, and multiple measurements are necessary for characterising non-linear effects. In one embodiment, a longitudinal array of sensors could be provided along the length of the body portion 14 such that the actual flow characteristics may be compared with various levels of accelerated flow characteristics along the longitudinal sensor array.

Isolating the Effects of Corrosion and/or Erosion

Measurements of metal loss are taken as described above. However, metal loss may be due to corrosion and/or erosion. It is desirable to isolate the effects of corrosion and erosion so as to provide disaggregated measurements of each. In the embodiment of FIG. 1, such isolation is enabled by the design of the shape of the body portion 14 and the locations of the sensors.

As mentioned above, the sensors 44 in the fourth sensor array 34 are subject to the same flow speed as the sensors 42 in the second sensor array 32 since the body portion 14 has the same cross-sectional area at these sensor array locations so that the same flow restriction is provided in each case. However, it is to be expected that the fourth sensor array 34 would be subject to much reduced (perhaps negligible) erosion and particle impacts as compared to the second sensor array 32 due to the angle of impingement of the flow on the body portion 14 at each sensor array. In particular, the flow is accelerating at the second sensor array 32 and the main flow (excluding turbulent effects) has a component directed towards the surface of the body portion 14, whereas the flow is decelerating at the fourth sensor array 34 and the main flow does not have a component directed towards the surface of the body portion 14. Thus, due to the tangential flow direction relative to the surface of the body portion 14 at the fourth sensor array 34, measurements taken at the fourth sensor array 34 are largely in the absence of particle impacts and largely in the absence of metal loss due to erosion. Thus, any metal loss at the fourth sensor array 34 is likely to be caused by corrosion alone. Hence, corrosion only measurements may be taken using the metal loss sensors in the fourth sensor array 34.

This enables the effects of erosion to be isolated by comparing the measurements from the second and fourth sensor arrays 32 and 34. In particular, the metal loss measurements of the fourth sensor array 34 (which relate to corrosion only) may be deducted from the metal loss measurements of the second sensor array 32 (which relate to corrosion and/or erosion). Thus, erosion only measurements may be inferred. However, it should be noted that these "erosion only" data will in fact also include the effects of so-called "erosion-corrosion".

It is also possible to take "corrosion only" measurements using metal loss sensors in the downstream sensor array 36 of the apparatus 10 shown in FIG. 2. In particular, the main flow (excluding any turbulence) is tangential to the surface of the body portion 14 at the downstream sensor array 36. Thus, it is to be expected that the downstream sensor array 36 would be subject to much reduced (perhaps negligible) erosion and particle impacts as compared to the first and second sensor arrays 31 and 32 due to the angle of impingement of the flow on the body portion 14 at each sensor array. Due to the tangential flow direction relative to the surface of the body portion 14 at the downstream sensor array 36, measurements taken at the downstream sensor array 36 are largely in the absence of particle impacts and largely in the absence of metal loss due to erosion. Thus, any metal loss at the downstream sensor array 36 is likely to be caused by corrosion alone. Hence, corrosion only measurements may be taken using the metal loss sensors in the downstream sensor array 36.

The effects of corrosion and erosion may also be isolated using metal loss sensors manufactured from different materials. For example, it is possible to sense erosion in the absence of corrosion using an ohmic resistance sensor constructed of a corrosion-resistant alloy steel. The deposition of conductive scales may also be sensed using such a sensor by comparing sensor results in the downstream portion against those in the accelerated region where scales are less likely to form. Such measurements may be compared with those taken using corrosion sensors based on ohmic resistance constructed of carbon steels, which would be subject to erosion and/or corrosion.

Conductive Scales

As mentioned above, it is possible to see the effects of conductive scales using electrical resistance based metal loss sensors. However, it can be difficult to distinguish the effects of conductive scales from the effects of corrosion and erosion. Therefore, in order to provide more accurate measurements of conductive scales, it is desirable to provide a separate conductive scales sensor which measures the effects of conductive scales using electrical impedance spectroscopy. In such sensors, corrosion resistant electrodes are provided and current is passed through at a number of different frequencies to detect deposition of conductive scales. Such techniques are well known in this field.

Stratified Flow

Use of similar sensors disposed annularly around the body portion 14 is particularly advantageous in the case of stratified flow where the type of flow varies in the vertical direction. For example, in an oil pipeline, there may be a shallow layer of water at the bottom of the pipe, followed by a layer of oil, and then gas filling the remainder of the pipe at the top. In addition, gravity will affect particles entrained in the fluid to some extent, and these variations may be measured using annularly disposed sensors.

Of course, it will be understood that the apparatus 10 could also be used to monitor turbulent flow characteristics.

Although preferred embodiments of the invention have been described, it is to be understood that these are by way of example only and that various modifications may be contemplated.

The invention claimed is:

1. An apparatus for characterising a flow through a conduit, the apparatus comprising:
a body portion having a longitudinal axis extending between first and second body portion ends, wherein the cross-sectional area of the body portion varies along the longitudinal axis, and wherein, in use, the body portion is arranged to be disposed substantially longitudinally within the conduit with the first body portion end disposed upstream of the second body portion end;
a first sensor disposed at or near the first body portion end; and
a second sensor longitudinally spaced from the first sensor, wherein the body portion has a larger cross-sectional area at the second sensor than at the first sensor such that, in use, the second sensor experiences an accelerated flow as compared to the first sensor;
wherein the first and second sensors are operable to sense a common variable, thereby enabling the effects of accelerated flow on the common variable to be characterised.

2. The apparatus of claim 1 wherein the second sensor is disposed at a location where the cross-sectional area of the body portion is largest.

3. The apparatus of claim 1 wherein the body portion comprises a substantially conical section.

4. The apparatus of claim 1 wherein the cross-sectional area of the body portion increases monotonically from the first body portion end to the second body portion end.

5. The apparatus of claim 1 wherein the cross-sectional area of the body portion increases monotonically from the first body portion end to a central portion and then decreases monotonically from the central portion to the second body portion end.

6. The apparatus of claim 1 wherein the first body portion end comprises an extended nose having a small cross-sectional area.

7. The apparatus of claim 1 wherein the body portion includes a longitudinal section having a substantially constant cross-sectional area.

8. The apparatus of claim 1 wherein the body portion is shaped such that the flow is substantially tangential to the body portion at the first and/or second sensors.

9. The apparatus of claim 1 wherein the body portion is shaped such that the flow is angled so as to impinge on the body portion at the first and/or second sensors.

10. The apparatus of claim 1 wherein the body portion is shaped so as to provide a smooth flow transition from the body portion to the downstream undisturbed flow.

11. The apparatus of claim 1 further comprising one or more additional sensors on the body portion, wherein the first, second and additional sensors are mutually longitudinally spaced along the body portion, and wherein the first, second and additional sensors are each operable to sense the common variable.

12. The apparatus of claim 1 wherein:
the first sensor is part of a first sensor array disposed at or near the first body portion end;
the second sensor is part of a second sensor array disposed at or near the longitudinal location of the second sensor; and
the first and second sensor arrays are operable to sense one or more common variables, thereby enabling the effects of accelerated flow on the one or more common variables to be characterised.

13. The apparatus of claim 12 wherein at least one of the first and second sensor arrays include sensors disposed at multiple angular locations around the body portion.

14. The apparatus of claim 1 wherein the first and second sensors are electrical resistance sensors, each arranged to provide a respective signal which varies in dependence upon electrical resistance of a respective target surface.

15. The apparatus of claim 14 wherein the target surfaces are either corrodible such that the provided signals vary in dependence upon corrosion of the respective target surfaces; or
corrosion-resistant such that the provided signals vary in dependence upon erosion of the respective target surfaces.

16. The apparatus of claim 1 wherein the first and second sensors are acoustic sensors, each arranged to provide a respective signal which varies in dependence upon acoustic noise generated by impacts of particles and fluid on a respective target surface, the target surfaces being acoustically decoupled from the body portion.

17. The apparatus of claim 1 wherein the first and second sensors together form a differential pressure transducer arranged to sense a pressure drop between the flow at the first sensor and the flow at the second sensor.

18. The apparatus of claim 1 further comprising at least one from the following group consisting of:
a temperature sensor arranged to sense a temperature of the flow at the first body portion end;
an absolute pressure transducer arranged to sense a pressure of the flow at the first body portion end;
a differential pressure transducer arranged to sense a pressure drop between the flow at the first body portion end and the flow at the second body portion end;
an acoustic sensor acoustically coupled to the body portion and arranged to provide a signal which varies in dependence upon the cumulative acoustic noise generated by impacts of particles and fluid on the body portion;
a solution conductivity sensor arranged to detect conductivity of the flow; and
a conductive scales sensor arranged to detect conductive scales using electrical impedance spectroscopy.

* * * * *